United States Patent [19]

Beck et al.

[11] Patent Number: 5,102,838

[45] Date of Patent: Apr. 7, 1992

[54] CATALYST FOR SELECTIVE OXIDATION REACTIONS

[75] Inventors: Horst-Philipp Beck, Dudweiler/Saar; Gerhard Emig, Erlangen; Günther Wiesgickl, Grosswallstadt; Karlheinz Burg; Karl-Friedrich Mück, both of Wiesbaden, all of Fed. Rep. of Germany

[73] Assignee: Hoechst Aktiengesellschaft, Frankfurt am Main, Fed. Rep. of Germany

[21] Appl. No.: 545,852

[22] Filed: Jun. 29, 1990

[30] Foreign Application Priority Data

Jun. 30, 1989 [DE] Fed. Rep. of Germany ....... 3921450

[51] Int. Cl.$^5$ .............................................. B01J 29/06
[52] U.S. Cl. .................................................. 502/60
[58] Field of Search ..................... 502/60, 79; 568/472

[56] References Cited

U.S. PATENT DOCUMENTS

| | | | |
|---|---|---|---|
| 3,013,985 | 12/1961 | Breck et al. | 502/79 |
| 3,382,039 | 5/1968 | Calmon et al. | 502/60 |
| 4,208,353 | 6/1980 | Webster et al. | 568/472 |
| 4,306,089 | 12/1981 | Webster et al. | 568/472 |
| 4,359,587 | 11/1982 | Abdurakhmanov et al. | 568/402 |
| 4,420,641 | 12/1983 | Gerberich et al. | 568/472 |
| 4,845,063 | 7/1989 | Chu | 502/60 |

FOREIGN PATENT DOCUMENTS

| | | |
|---|---|---|
| 113173 | 5/1975 | Fed. Rep. of Germany . |
| 2816471 | 10/1978 | Fed. Rep. of Germany . |
| 3037536 | 7/1986 | Fed. Rep. of Germany . |
| 165039 | 10/1982 | Japan ............... 502/60 |
| 1603821 | 12/1981 | United Kingdom . |

*Primary Examiner*—Carl F. Dees

[57] ABSTRACT

Silicate catalysts which can be employed for selective oxidation reactions of organic substances, a process for the preparation of these catalysts and their use are described.

The catalyst is distinguished by high long-term activity, by the reaction temperature required for the reaction being lower in comparison with catalysts composed of pure silver and by higher conversions and selectivities in the oxidative dehydrogenation of alkanols in comparison with pure silver or silver on supports.

13 Claims, No Drawings

CATALYST FOR SELECTIVE OXIDATION REACTIONS

DESCRIPTION

The invention relates to silicate catalysts which can be employed for selective oxidation reactions of organic substances, to a process for the preparation of these catalysts and to their use.

Skeleton silicate catalysts, for example zeolites, are already employed on a large industrial scale as catalysts for the non-oxidative conversion of hydrocarbons, for example in catalytic cracking.

It is also known that organic compounds can be oxidized selectively by means of zeolite catalysts, as is the case, for example, in the manufacture of acetone from propene. In this case a selectivity of 90% is achieved at a conversion of 50%. No statements are made concerning the long-term activity and the aging behavior of the catalysts used.

It is also assumed that, because of their special structure, zeolites tend to accelerate the total oxidation of organic compounds to $CO_2$ and water.

The preparation of certain catalysts based on zeolites is described in East German Patent 113,173. In this case certain metals, such as vanadium and/or titanium, are incorporated into the zeolites by ion exchange.

A "silver-on-pumice" or "silver-on-$Al_2O_3$" catalyst is frequently used for the oxydehydrogenation reactions of $C_1$–$C_4$-alcohols, for example of methanol to give formaldehyde, which are of particular industrial importance. The preparation of a silver catalyst synthesized by impregnating the support, composed of $Al_2O_3$ and $SiO_2$ in the form of cristobalite, with silver nitrate solution is discussed in German Patent 3,037,536. A catalyst composed of a metal or ceramic support which has been coated or impregnated with metallic copper, silver, gold or iron (German Offenlegungsschrift 2,816,471) is also described for the preparation of formaldehyde.

However, the catalysts mentioned, which are employed in processes for the preparation of carbonyl compounds by the oxidative dehydrogenation of $C_1$–$C_4$-alcohols, give only relatively low yields of end product, relative to the throughput and conversion of raw material; in addition the degree of conversion of the raw material and the quality of the products is still unsatisfactory in most cases. Formic acid is also frequently formed as an undesirable by-product in the known processes.

It was therefore the object to find other catalyst substances by means of which the process for the preparation of oxo compounds is improved further.

The invention therefore relates to a complex silicate catalyst having the formula M $\cdot v$ Ag$^0\cdot w$ AgX·Al$_2$O$_3$·$x$ SiO$_2$·$y$ H$_2$O  (1)

in which M denotes a metal atom of valence n, Ag$^0$ denotes elementary silver, X denotes a halogen atom and v, w, x and y denote stoichiometric coefficients. Elements of the first and second main group of the periodic system, preferably sodium, potassium, calcium and barium, are used as the metals M. The H$^+$ or NH$_4^+$ forms can also be present in the silicate instead of the metals M$^{n+}$. The NH$_4^+$ form is converted into the H$^{n+}$ form at high reaction temperatures. The halogen atom X employed is bromine, but preferably chlorine. The coefficients v, w, x and y represent numbers from 0.1 to 7.5, preferably to 4.6. A particularly preferred silicate complex has the formula $$Na_2O \cdot 1.4\ Ag \cdot 0.4\ AgCl \cdot Al_2O_3 \cdot 2.47\ SiO_2 \cdot 3.9\ H_2O \qquad (2)$$

The invention also relates to a process for the preparation of the complex silicate catalyst, in which (a) a skeleton silicate is reacted with a silver salt, (b) the skeleton silicate containing silver ions is converted by means of reducing agents into a skeleton silicate complex containing elementary silver, (c) this complex is converted by partial re-oxidation with oxidizing agents into a silicate complex containing silver(I) ions and elementary silver and (d) the complex is then converted into a silicate complex of the formula (1) by treatment with a solution containing halide ions in an alkaline medium.

Zeolites which are generally customary can be used as skeleton silicates for the preparation of the catalysts according to the invention. Particularly suitable examples of silicates of this type are products marketed commercially such as 6 $Na_2O \cdot 6\ Al_2O_3 \cdot 12\ SiO_2 \cdot 12\ H_2O$, known as molecular sieve ZA (manufacturer: Union Carbide, USA) and also $Na_{1.8}H_{0.2}O \cdot Al_2O_3 \cdot 4.65 SiO_2 \cdot 10.4 H_2O$, known as Baylith CP 190 (manufacturer: Bayer AG, Leverkusen, West Germany). The water content of the zeolites is subject to considerable variations. It is preferable to use $Na_2O \cdot Al_2O_3 \cdot 2.47\ SiO_2 \cdot 3.9\ H_2O$, known as molecular (manufacturer: Union Carbide, Corp., New York, USA).

Solutions containing silver cations are employed for doping, i.e. for inclusion into the skeleton silicates. The molar silver ion concentration is 0.001 to 10, preferably 0.01 to 1, mol/liter. The reaction is carried out at room temperature, i.e. at 20°–30° C., with stirring and with the exclusion of light. The treatment of the skeleton silicate with the solution of silver ions can be repeated until the desired degree of exchange for the metal ions of the skeleton silicate has been obtained. For the subsequent reaction the doped silicate is dried. A similar loading can also be obtained, for example, in the impregnation process.

The silver ions contained in the skeleton silicate are then converted into elementary silver by means of reducing agents. This reduction is carried out, for example, in a customary manner by means of hydrogen at temperatures between 100 and 500° C., preferably between 300 and 400° C. The partial pressure of the reducing agent is 0.05 to 5.0 bar, preferably 0.4 to 0.75 bar, the falling partial pressure being a measure of the reduction.

The partial re-oxidation of stage (c) is carried out by means of oxidizing agents, for example oxygen or a halogen, such as bromine or chlorine. In this reaction the elementary silver is partially converted into silver(I) ions or silver halide with the elimination of water or hydrogen halide. The reaction takes place at temperatures between 100 and 350° C., preferably 250 to 290° C., and in the case of a halogen preferably between 100 and 200° C., under a partial pressure of 0.05 to 5.0 bar, preferably 0.4 to 0.75 bar. The treatment time for the oxidation extends from 5 to 60, preferably 10 to 30, minutes.

In stage (d) the resulting silicate complex is treated with an aqueous solution containing halide ions, preferably chloride. The molar concentration of this solution is 0.001 to 2, preferably 0.01 to 0.5. It is preferable to employ hydrogen halide acids, such as hydrochloric acid or hydrobromic acid, for this purpose. The treatment is carried out within a period of 2 to 15, preferably 5 to 10, minutes. A silver ion complex-former, for example ammonia in a 0.1 to 0.3 molar solution, is then added. An excess of a salt containing the metal cation M in equation (1), for example $NaNO_3$, is added at the same time. The suspension is then stirred for 20 to 50 minutes. The digestion with the complex-former and the salt can be repeated several times.

If the oxidation is carried out with a halogen, the treatment with a solution containing halide ions becomes unnecessary. The after-treatment in stage (d) is then only carried out with an alkaline solution of a complex-former in the presence of the metal salt.

After drying, the resulting catalyst is processed into pellets measuring 1 to 5 mm and is then ready for use.

As a result of the precipitation of the silver, which is partly present in the ionic form, as halide and the partial washing out of the latter by means of complex-formers, an elementary silver component which is surprisingly active and selective in action remains in the silicate matrix. The catalyst prepared in this way is distinguished by a high long-term activity, by the reaction temperature required for the reaction being lower in comparison with catalysts composed of pure silver and by higher conversions and selectivities in the oxidative dehydrogenation of alkanols, for example methanol to give formaldehyde, in comparison with pure silver or silver on supports.

The catalyst according to the invention is used in oxydehydrogenation reactions. It is particularly suitable for the oxydehydrogenation of alkanols having 1 to 4 carbon atoms in the alkyl radical and particularly in the oxidative dehydrogenation of methanol to give formaldehyde as described in German Patent Application P 39 21 452.4, entitled: "Process for the preparation of carbonyl compounds", which has been filed on the same day and to which reference is hereby made.

EXAMPLES 1) 10.71 g of zeolite 13× (formula: $Na_2O \cdot Al_2O_3 \cdot 2.47 SiO_2 \cdot 3.9 H_2O$) were put into a beaker, 500 ml of 0.1N $AgNO_3$ solution were added and the mixture was stirred vigorously for 4 hours with the exclusion of light. After filtration, the residue was washed with 50 ml of water and a further 400 ml of 0.1N silver nitrate solution were added, the mixture was stirred for 4 hours with the exclusion of light and then filtered and the resulting solid substance was dried in the air. 7.88 g of this substance were freed from water under reduced pressure at 350° C. and were then subjected to reductive treatment with hydrogen under a pressure of 0.6 bar for 20 minutes at the same temperature. The hydrogen was then removed and the residue was cooled to 270° C. The solid substance was then treated in oxygen (0.67 bar) for 8 minutes at this temperature and, after the oxygen had been removed, was cooled to approx. 25° C. 3.5 g of this resulting substance were suspended in 200 ml of water, and 5 ml of concentrated hydrochloric acid were added with stirring. Five minutes later 25 ml of half-concentrated ammonia solution (7 mol/liter) and 17 g of sodium nitrate were metered in. This suspension was stirred for 1 hour and then filtered, and the residue was washed with a total of 200 ml of water. The substance obtained was dried in the air and compressed into pellets of 6 mm diameter which were subsequently comminuted.

2) 8.51 g of zeolite 13× (formula: $Na_2O \cdot Al_2O_3 \cdot 2.47 SiO_2 \cdot 3.9 H_2O$) were put into a beaker, 400 ml of 0.1N $AgNO_3$ solution were added and the mixture was stirred vigorously for 3 hours with the exclusion of light. After filtration, the residue was washed with 50 ml of water and a further 400 ml of 0.1N silver nitrate solution were added, the mixture was stirred for 3 hours with the exclusion of light and then filtered, and the resulting solid substance was dried in the air. 6.35 g of this substance were freed from water under reduced pressure at 330° C. and were then reduced for 25 minutes with hydrogen under a pressure of 0.67 bar. The substance was then cooled to 170° C. under reduced pressure, oxidized with chlorine under a pressure of 0.6 bar for 30 minutes and cooled to room temperature under reduced pressure. 4 g of the substance obtained were suspended in 200 ml of water, and 20 g of sodium nitrate and 30 ml of half-concentrated ammonia solution were metered in. This suspension was stirred for 20 minutes and then filtered and the residue was washed with a total of 250 ml of water. The substance obtained was dried in the air and compressed into pellets of 6 mm diameter, which were subsequently comminuted.

We claim:

1. A silicate catalyst of the formula $$M \cdot v \, Ag^0 \cdot w \, AgX \cdot Al_2O_3 \cdot x \, SiO_2 \cdot y \, H_2O \quad (1)$$

in which M denotes a metal atom of valence n, $Ag^0$ denotes elementary silver, X denotes a halogen atom and v, w, x and y denote stoichiometric coefficients.

2. A catalyst as claimed in claim 1, which corresponds to the formula $$Na_2O \cdot 1.4 \, Ag \cdot 0.4 \, AgCl \cdot Al_2O_3 \cdot 2.47 \, SiO_2 \cdot 3.9 \, H_2O \quad (2)$$

3. A process for the preparation silicate catalyst of claim 1, wherein (a) a framework is reacted with a silver salt, (b) the framework silicate containing silver ions is converted by means of reducing agents into a silicate complex containing elementary silver, (c) this complex is converted by partial re-oxidation with oxidizing agents into a silicate complex containing silver(I) ions and elementary silver and (d) the complex is then converted into a silicate complex of the formula (1) by treatment with a solution containing halide ions in an alkaline medium.

4. The process as claimed in claim 3, wherein the reducing agent used is hydrogen.

5. The process as claimed in claim 3, wherein the oxidizing agent employed is oxygen or a halogen, and hydrogen or hydrogen halide is liberated in the course of the re-oxidation.

6. The process as claimed in claim 5, wherein the oxidizing agent employed is chlorine.

7. The process as claimed in claim 3, wherein, when the re-oxidation is carried out with a halogen in stage (c), the subsequent treatment (d) is only carried out with an alkaline solution of a complex-former in the presence of a salt containing the metal ion M of formula (1).

8. The process as claimed in claim 3, wherein the silver(I) ions formed in the complex in stage (c) are present in the form of silver chloride.

9. The process as claimed in claim 3, wherein the framework silicate is treated in stage (a) with a solution containing $Ag^+$ ions in a concentration of 0.001 to 10 mol/liter, at room temperature, with the exclusion of light.

10. The process as claimed in claim 3, wherein the reduction in stage (b) is carried out at 100 to 500° C., under a partial pressure of the reducing agent of 0.05 to 5.0 bar.

11. The process as claimed in claim 3, wherein the reoxidation in stage (c) is carried out at 100 to 350° C., under a partial pressure of the oxidizing agent of 0.05 to 5.0 bar, in the course of 5 to 60 minutes.

12. The process as claimed in claim 11, wherein the reoxidation is carried out using a halogen as the oxidizing agent, at 100°–200° C.

13. The process as claimed in claim 3, wherein the solution containing halide ions in stage (d) has a molar concentration of 0.00I to 2.

* * * * *

UNITED STATES PATENT AND TRADEMARK OFFICE
CERTIFICATE OF CORRECTION

PATENT NO. : 5,102,838

DATED : April 7, 1992

INVENTOR(S) : Horst-Philipp Beck, et al

It is certified that error appears in the above-identified patent and that said Letters Patent is hereby corrected as shown below:

In column 1, at line 56, "M" should read $--M^{n+}_{2/n} O--$.

In column 2, at line 29, insert after "molecular", --sieve Z13X--.

IN THE CLAIMS

In claim 1, column 4, line 23 "M" should read $--M^{n+}_{2/n} O--$.

In claim 3, column 4, line 34, after "preparation" insert --of a--;

UNITED STATES PATENT AND TRADEMARK OFFICE
CERTIFICATE OF CORRECTION

PATENT NO. : 5,102,838

DATED : April 7, 1992

INVENTOR(S) : Horst-Philipp Beck, et al

It is certified that error appears in the above-identified patent and that said Letters Patent is hereby corrected as shown below:

In claim 3, column 4, line 35, after "framework" insert --silicate--.

In claim 13, column 6, line 5, change "0.00I" to --0.001--.

Signed and Sealed this

Third Day of August, 1993

Attest:

MICHAEL K. KIRK

Attesting Officer     Acting Commissioner of Patents and Trademarks